(12) United States Patent
Morhain et al.

(10) Patent No.: US 10,532,121 B2
(45) Date of Patent: Jan. 14, 2020

(54) DEVICE FOR EVAPORATING VOLATILE SUBSTANCES

(75) Inventors: Cedric Morhain, Trento (IT); Walter Sordo, Trento (IT); Stefano Deflorian, Trento (IT)

(73) Assignee: ZOBELE HOLDING SPA, Trento (IT)

( * ) Notice: Subject to any disclaimer, the term of this patent is extended or adjusted under 35 U.S.C. 154(b) by 0 days.

(21) Appl. No.: 14/233,919

(22) PCT Filed: Jul. 20, 2012

(86) PCT No.: PCT/EP2012/064296
§ 371 (c)(1),
(2), (4) Date: Feb. 13, 2014

(87) PCT Pub. No.: WO2013/014078
PCT Pub. Date: Jan. 31, 2013

(65) Prior Publication Data
US 2014/0166774 A1    Jun. 19, 2014

(30) Foreign Application Priority Data
Jul. 22, 2011    (EP) ..................................... 11175003

(51) Int. Cl.
*A61L 9/12*    (2006.01)

(52) U.S. Cl.
CPC ........... *A61L 9/12* (2013.01); *A61L 2209/131* (2013.01)

(58) Field of Classification Search
CPC .. A61L 9/12; A61L 2209/131; A61L 2439/40; A61L 9/127; A01M 1/2033; A01M 1/2044; A01M 1/2077; B32B 25/10; B32B 2439/40

USPC .................................... 239/34, 44, 53, 55, 56
See application file for complete search history.

(56) References Cited

U.S. PATENT DOCUMENTS

| | | | | |
|---|---|---|---|---|
| 4,356,969 A | * | 11/1982 | Obermayer et al. ............... 239/6 |
| 4,849,606 A | * | 7/1989 | Martens et al. ............... 392/390 |
| 4,874,129 A | * | 10/1989 | DiSapio et al. ................. 239/36 |
| 5,395,047 A | * | 3/1995 | Pendergrass, Jr. ............... 239/56 |
| 5,439,100 A | * | 8/1995 | Gordon et al. ..................... 206/5 |
| 5,993,954 A | * | 11/1999 | Radovanovic ............ B32B 5/22 428/315.5 |
| 2003/0089791 A1 | * | 5/2003 | Chen ................... A01M 1/2077 239/35 |
| 2004/0057975 A1 | * | 3/2004 | Maleeny et al. ............... 424/401 |
| 2006/0196965 A1 | * | 9/2006 | Christianson ........ A47G 1/0616 239/60 |
| 2010/0270392 A1 | * | 10/2010 | Trent et al. ...................... 239/55 |

OTHER PUBLICATIONS

International Search Report issued in counterpart PCT Application No. PCT/EP2012/064296.

* cited by examiner

*Primary Examiner* — Steven J Ganey
(74) *Attorney, Agent, or Firm* — Lucas & Mercanti, LLP

(57) ABSTRACT

The invention refers to a device for evaporating volatile substances comprising: a container of a liquid volatile substance, and a vapour permeable membrane (1) and a thermoplastic porous or fibrous laminate (2) bonded together. Said container is closed at its opening by said vapour permeable membrane (1) and the fibrous laminate (2), wherein the fibrous laminate (2) is welded to the thermoformed part of the container.

12 Claims, 3 Drawing Sheets

DEVICE FOR EVAPORATING VOLATILE SUBSTANCES

CROSS REFERENCE TO RELATED APPLICATION

This Application is a 371 of PCT/EP2012/064296 filed on Jul. 20, 2012, which claims the priority of European Patent Application No. 11175003.0 filed on Jul. 22, 2011, both applications are incorporated herein by reference in their entirety.

OBJECT OF THE INVENTION

The present invention relates in general to devices for evaporating volatile substances, in particular for volatile substances having complex chemical compositions for example some types of perfumes and/or insecticides.

More in particular, the present invention refers to a reinforced membrane structure, in which a semi-permeable membrane is laminated with a fibrous laminate or a capillary laminate.

BACKGROUND OF THE INVENTION

Evaporator devices for volatile substances are very well-known, for diffusing air fresheners, pesticides or similar chemical substances.

Are well known in the market containers containing volatile substances such as insecticide or fragrances that are closed by a semi-permeable membrane. Most of these products include a polyolefin monolithic membrane. Due to high selectivity of polyolefins, and the complexity of some volatile substances (very complex fragrances compositions), these products generally have a quite low evaporation rate and accept a limited number of fragrances with quite simple fragrances compositions (with low quality).

Several intends have been done to try to solve these drawbacks. On one side, the use of microporous films allows a much lower selectivity of the fragrance through the membrane and thus a higher evaporation rate of a higher quality fragrance. Nevertheless, the transport of fragrances through this kind of membrane is by capillarity that is a process that is driven by pressure and the product may leaks in some conditions.

On the other side, transport through monolithic membranes is driven by gradient concentration, so if the fragrance on the external side of the membrane do not evaporate, no more fragrance is transported through the membrane and the fragrances cannot leaks.

Several materials have been proposed but most of them have elastomeric characteristics. This gives the advantage of a higher permeability of fragrances through these materials. The problem with these membranes is that permeation through the membrane is done partially by solubilisation of the liquid in the membrane material, that mean, how much liquid is able to contain a certain volume of membrane material. So, the higher the solubility the higher the permeability. Nevertheless, there is a price to pay for that and that is that the elastomeric membrane material use to swell, that provokes wrinkles on the surface and decrease its mechanical strength.

This negative effect is completely linked to the chemical nature of the volatile substance so the same product with different fragrances may present several different level of this defect.

Additionally, this kind of membrane product use to come with a barrier top aluminium layer that has to be pealed off before first use. In the case of elastomeric materials, these materials use to have already quite lower mechanical resistance vs polyolefins, that could be even lower due to the chemical solubilisation. This may provoke a membrane rupture when aluminium is peeled off.

Finally, in the case of monolithic membranes, permeability use to be related to the amount of surface of the membrane that is in contact with the liquid. This has 2 consequences:

As refill is not completely full, the maximum evaporation surface is never used.

As liquid level decreases with time, the evaporation rate decrease proportionally along device life.

DESCRIPTION OF THE INVENTION

One object of this invention, is to solve the previously described drawbacks of the prior art, in a simple and economic manner.

The invention provides a multilayered structure for a membrane, which comprises a thermoplastic fibrous laminate bonded to a monolithic vapour permeable membrane. In the present invention the term fibrous laminate is to be understood as any type of thermoplastic material having a capillary or porous structure, and which strength is suitable to act as a substrate to reinforce the membrane.

The invention also refers to a manufacturing process of the device, in which the multilayer membrane is welded to a container in such a way the thermoplastic fibre structure is erased completely by the welding and a monolithic film of the material is created in the welding area.

Fibrous laminate is placed on the inner side of the container. Fibre structure is erased in the area of welding in order to avoid liquid can pass between container and membrane.

The container with the multilayered structure according to the present invention, can be used in conjunction with any type of device for evaporating volatiles substances, for example an evaporating device incorporating heating means or using a forced flow of air to enhance the evaporation.

Whatever kind of material is used for the semipermeable membrane, it is critical that the fibrous laminate is:

made from a thermoplastic material, optimally completely of thermoplastic material has a melting point lower than the membrane material.

With the structure of the invention several advantages are achieved:

On one side, the membrane is mechanically reinforced by the fibrous laminate, avoiding thus the wrinkles and increasing the strength that the membrane can support, and thus reducing the possibility of rupture when the top barrier material is peeled off.

Then, as the lamina is fibrous it has capillary properties, for that the fibrous laminate distributes liquid all over the internal surface of the membrane with the liquid. This way, it is assured that 100% of the evaporation surface of the membrane is used at any time.

As the fibrous lamina is porous, it does not represent any limit to liquid transport through the membrane.

DESCRIPTION OF THE DRAWINGS

To complete the description that is being made and with the object of assisting in a better understanding of the characteristics of the invention, in accordance with a preferred example of practical embodiment thereof, is a set of drawings wherein by way of illustration and not restrictively, the following has been represented.

PREFERRED EMBODIMENTS OF THE INVENTION

Figure 1:
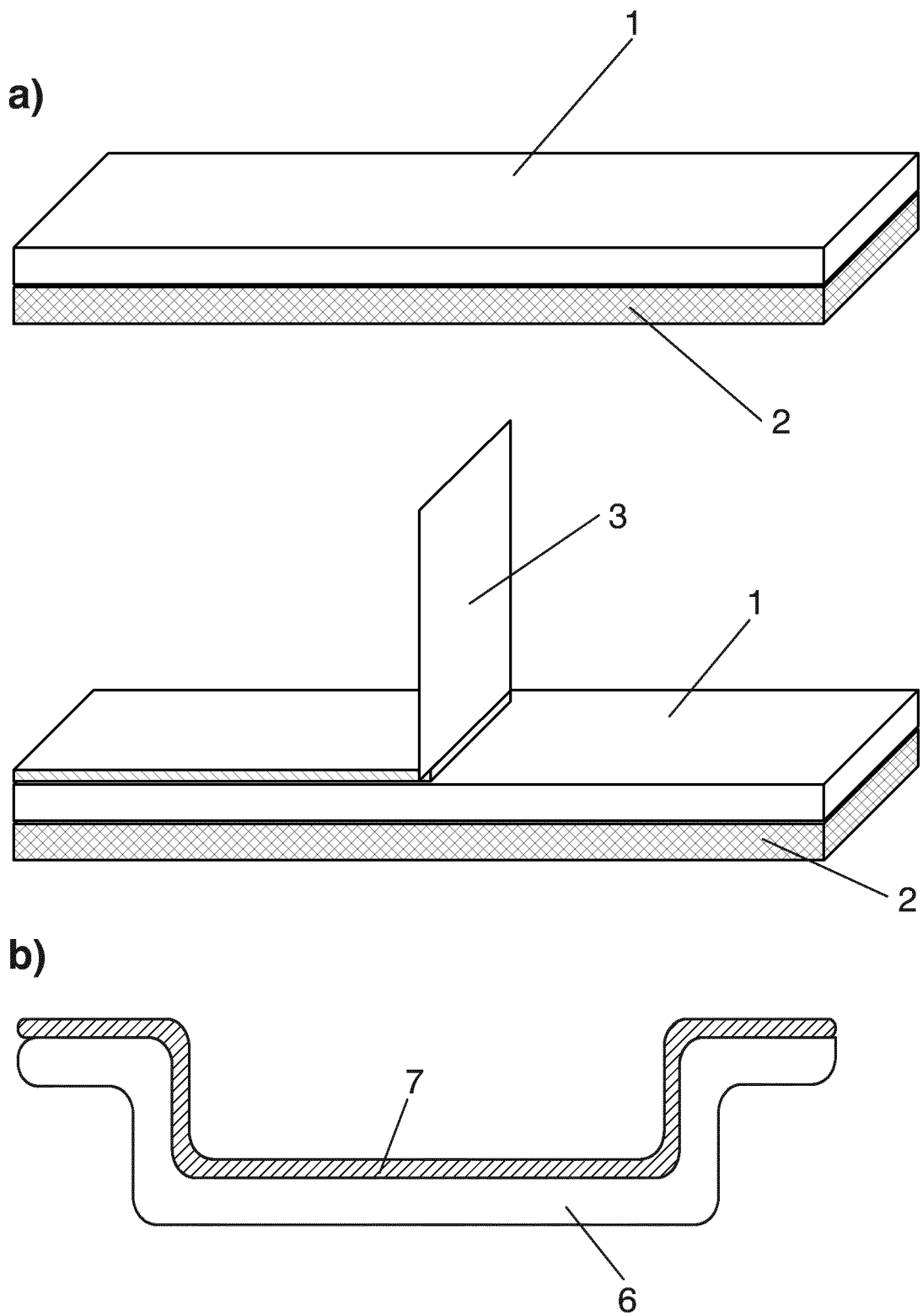
FIG. 1—drawing (a) shows a perspective view of a schematic representation of the multilayered membrane of the invention formed by a thermoplastic fibrous laminate bonded to a monolithic vapour permeable membrane, and drawing (b) is a similar representation than figure (a) with a removable barrier film over the membrane, and provided above a container prior to the welding process.

The device for evaporating volatile substances of the invention, in a preferred embodiment comprises a container (6) of a liquid volatile substance (8), with an opening (10) and at least a part of the container in the periphery of said opening made of a thermoformed material.

The device further comprises a vapour permeable membrane (1) and a thermoplastic fibrous laminate (2) bonded together, so that the container is closed by said vapour permeable membrane (1) and the fibrous laminate (2), in such a manner that the fibrous laminate (2) is welded to the thermoformed part of the container.

A film of a sealing material (7) compatible with the fibrous laminate, is provided on the internal surface of the container and on a perimetral lip (11) of the container around the opening (10).

During the manufacturing process, the sandwiched structure formed by the membrane (1), laminate (2) and barrier (3), is placed on the perimetral lip (11) closing the container as shown in FIG. 2b, so that the laminate (2) is arranged internally to the container. In the welding process, heat and pressure is applied by a sealing flange (4) of a sealing tool, to the periphery of the membrane structure, until the perimetral part of the thermoplastic laminate fuses with the container forming thereby a sealing ring (9), which prevent any liquid leak to the outside.

Figure 3:
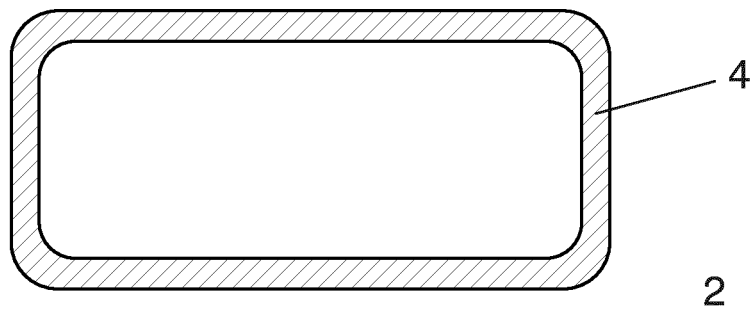
FIG. 3—shows schematically the effect of the manufacturing process of the invention, wherein drawing (a) shows a plan view of a sealing flange of a sealing tool used for welding the multilayered membrane to a container; drawing (b) shows a plan view of the multilayered membrane before welding; and drawing (c) shows a plan view of the multilayered membrane after welding, wherein it has been represented how the area of the membrane to which the sealing flange has been applied has a different appearance because the fibrous material is erased because it has been fused.
Figure 3:
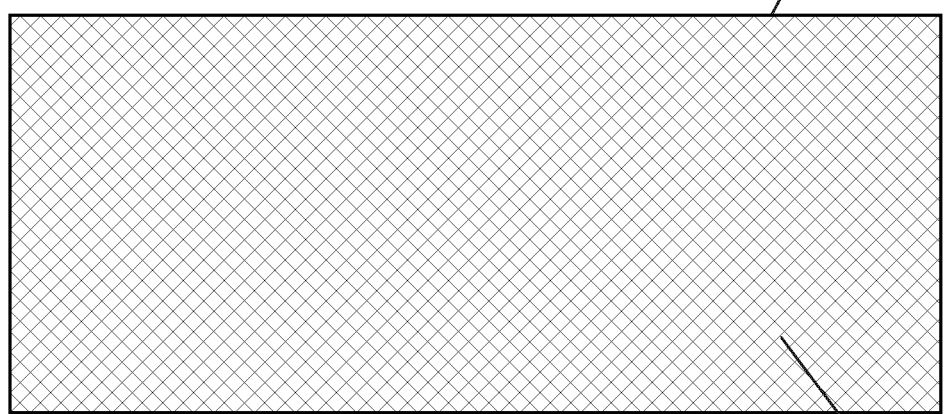
Figure 3:
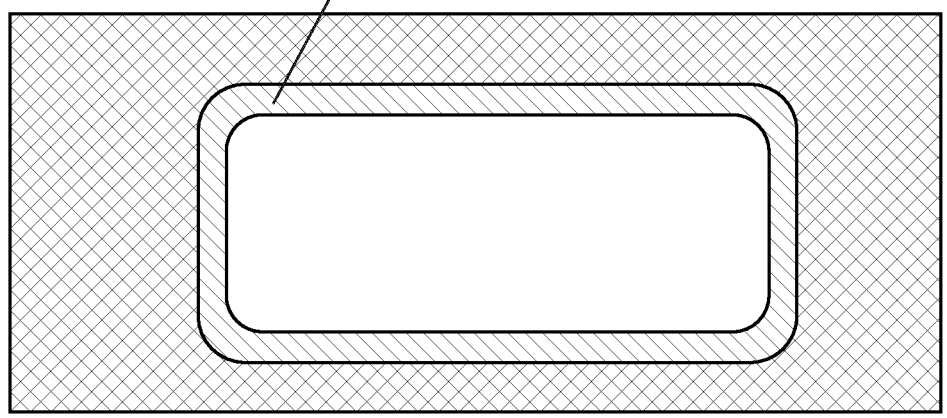

As shown in FIG. 3c, the area of the fibrous laminate that has been erased in the welding process, change its visual appearance and this effect is used in the present invention to determine the quality of the welding process.

Figure 2:
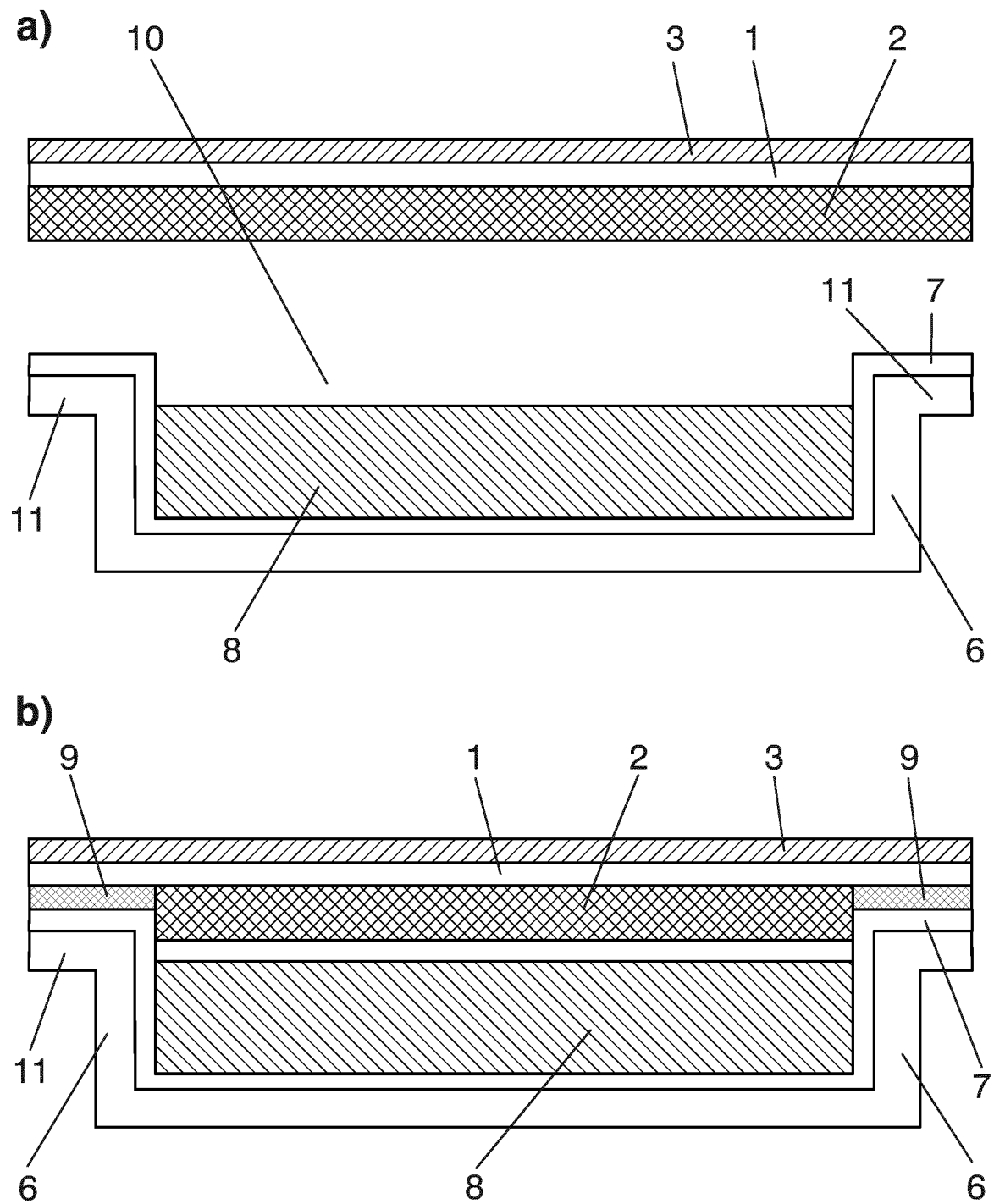
FIG. 2—drawing (a) is an schematic elevational view of the membrane structure placed above a container prior to the welding process, and drawing (b) is a similar representation than drawing (a) once the membrane structure has been welded to the container.

FIG. 2 shows the container in a non-operative position (horizontally). However, in use the device, would the place in another position (for example vertically) so that the liquid volatile substance (8) is in contact with the fibrous laminate (2) and it can evaporate through the membrane.

Preferably, the membrane is a monolithic membrane with elastomeric behaviour, for example an elastomeric polyester, polyamide block ether or polyurethane or Polyolefin elastomer.

The fibrous substance can be whatever fabric made of a thermoplastic material (a plastic that can be molten).

Preferably it is a non woven material, or a polyolefin non woven, or a PP or PE non woven, or an hybrid PP/PE non woven where fibre has a PP core and a PE shell. Alternatively, the laminate may consist of a laminate of open foam.

The lamination between the membrane and the fibrous material can be done without any adhesive, by thermally/mechanically bonding the two layers, but preferably, the adhesion is done by applying an adhesive.

Preferably, the adhesive is applied in a discrete form (not a continuous layer), by points, or by lines, in order to avoid the adhesive decrease the permeation speed (acts as a barrier). The adhesive, may also be applied in the form of a thin continuous layer of adhesive made of material permeable to the volatile substance.

Preferably the container is made of a thermoformed material, wherein the upper layer of this material is made of a material compatible with the fibrous laminate. Optimally it is the same, so that, in case the fibrous laminate is a non woven made of PE or hybrid PP/PE (as described above), the upper layer of the container will be done of PE as well.

The device also incorporates an aluminium foil (3) with a plastic layer on the side of the membrane, that is partially compatible with the membrane material, that means, that can bonds to the membrane but not in a permanent way. The aluminium foil (3) avoids evaporation of the volatile substance before the first use.

Example 1

Membrane is a polyester elastomer of 70 microns thickness.

Adhesive is a poluyrethane solventless based adhesive applied in crossed lines.

Non woven is a PE spunbound non woven of 50 g/m2.

Thermoformed container is made of PET/EVOH/PE.

Example 2

Membrane is a polyester elastomer of 70 microns thickness.

Adhesive is a poluyrethane solventless based adhesive applied in a thin continuous layer.

Non woven is a PE spunbound non woven of 50 g/m2.

Thermoformed container is made of PET/EVOH/PE.

The invention claimed is:

1. A device for evaporating volatile substances comprising:
   a first portion comprising a container having a volume adapted to hold a liquid volatile substance, the first portion comprising a peripheral part and an opening that provides access to the volume, the first portion further comprising a first layer of a thermoformed material and a second layer of a sealing material, the second layer of the sealing material having a first surface located on the peripheral part and a second surface within the volume, and
   a second portion comprising a vapour permeable membrane and a fibrous laminate bonded together, wherein the fibrous laminate is a reinforcing substrate adapted to reinforce the vapour permeable membrane,
   wherein the fibrous laminate of the second portion is welded to the peripheral part of the first portion,
   wherein said first portion is closed at the opening by said second portion, thereby enclosing the volume, wherein the fibrous laminate extends through the opening, is in contact with the second surface of the sealing material within the volume, and fills a part of the volume, wherein the liquid volatile substance is disposed in the volume, wherein the fibrous laminate is arranged in contact with the liquid volatile substance so that the liquid volatile substance evaporates through the vapour permeable membrane.

2. The device according to claim 1 wherein the fibrous laminate is selected to have a melting point lower than the melting point of the vapour permeable membrane.

3. The device according to claim 1 wherein the vapour permeable membrane is an elastomeric monolithic membrane.

4. The device according to claim 3 wherein the elastomeric monolithic membrane comprises a material selected from the group comprising: an elastomeric polyester, polyamide block ether, polyurethane, and polyolefin elastomer.

5. The device according to claim 1 wherein the fibrous laminate is selected from the group comprising: non woven material, polyolefin non woven, polypropylene or polyethylene non woven.

6. The device according to claim 5 wherein the fibrous laminate includes a non woven material made of fibers with a polypropylene core and a polyethylene shell.

7. The device according to claim 1 wherein the vapour permeable membrane and the fibrous laminate are laminated together by thermally and mechanically bonding these two elements.

8. The device according to claim 1 wherein the vapour permeable membrane and the fibrous laminate are laminated together by applying in a discrete form an adhesive in between.

9. The device according to claim 1 wherein the vapour permeable membrane and the fibrous laminate are laminated together by applying in between of a continuous layer of an adhesive material which is permeable to the volatized substances.

10. The device according to claim 1 wherein the fibrous laminate is a polyethylene spunbound non woven having a grammage within the range 50 to 150 g/m2.

11. The device according to claim 1 wherein the container is a thermoformed container made of polyethylene terephthalate/polyethylene vinyl alcohol/polyethylene.

12. The device according to claim 1 wherein a removable barrier film is provided on the outer surface of the vapour permeable membrane.

* * * * *